United States Patent [19]
Tonariya et al.

[11] Patent Number: 5,518,711
[45] Date of Patent: May 21, 1996

[54] X-RAY CONTRAST MEDIUM COMPRISING BARIUM AND XANTHAN GUM FOR EXAMINATION OF LARGE INTESTINE AND SMALL INTESTINE

[75] Inventors: Yoshito Tonariya, Tokyo; Hiroaki Shimizu, Yamanashi; Yukihito Wada, Saitama; Kazuhiro Yamaguchi, Higashimatsuyama; Tomio Yamasaki; Michiyuki Ishii, both of Saitama; Yoichi Tojima, Urawa; Mitsuo Togashi, Oyama; Yukihiro Noguchi, Omiya, all of Japan

[73] Assignee: Ohta Seiyaku Kabushiki Kaisha, Saitama, Japan

[21] Appl. No.: 240,762

[22] PCT Filed: Sep. 28, 1993

[86] PCT No.: PCT/JP93/01375

§ 371 Date: May 17, 1994

§ 102(e) Date: May 17, 1994

[87] PCT Pub. No.: WO94/07540

PCT Pub. Date: Apr. 14, 1994

[30] Foreign Application Priority Data

Oct. 2, 1992 [JP] Japan .................................. 4-302811

[51] Int. Cl.⁶ .................................................. A61K 49/04
[52] U.S. Cl. .......................... 424/9.411; 424/709; 514/54
[58] Field of Search ........................... 424/4, 709, 9.411; 514/54

[56] References Cited

U.S. PATENT DOCUMENTS

| | | | |
|---|---|---|---|
| 3,784,681 | 1/1974 | Fischler | 424/4 |
| 5,160,724 | 11/1992 | Tonariya et al. | 424/4 |
| 5,281,408 | 1/1994 | Unger | 424/4 |

FOREIGN PATENT DOCUMENTS

| | | |
|---|---|---|
| 0360266 | 3/1990 | European Pat. Off. . |
| 0526862 | 2/1993 | European Pat. Off. . |
| 54-34057 | 10/1979 | Japan . |
| 57-53765 | 11/1982 | Japan . |
| 2-85217 | 3/1990 | Japan . |

*Primary Examiner*—Gary E. Hollinden
*Attorney, Agent, or Firm*—Birch, Stewart, Kolasch & Birch

[57] ABSTRACT

This invention provides an X-ray contrast medium for examination of the large and the small intestine comprising an aqueous suspension containing 15 to 35 w/v % of barium sulfate and 0.6 to 0.15 w/v % of xanthan gum, wherein when the barium sulfate concentration is in the range of 15 to 20 w/v %, the amount of xanthan gum used is in the range of 0.3 to 0.6 w/v %; when the barium sulfate concentration is in the range of 20 to 30 w/v %, the amount of xanthan gum used is in the range of 0.2 to 0.5 w/v %; and when the barium sulfate concentration is in the range of 30 to 35 w/v %, the amount of xanthan gum used is in the range of 0.15 to 0.4 w/v %, and wherein, in each case, the higher the barium sulfate concentration is, the smaller the amount of xanthan gum used is; and the lower the barium sulfate concentration is, the larger the amount of xanthan gum used is.

4 Claims, 8 Drawing Sheets

X-RAY CONTRAST MEDIUM COMPRISING BARIUM AND XANTHAN GUM FOR EXAMINATION OF LARGE INTESTINE AND SMALL INTESTINE

TECHNICAL FIELD

This invention relates to a barium sulfate contrast medium for use in X-ray examination by double contrast method of the large and small intestines, and also in computed tomography (X-ray CT) of the large intestine, practiced in the medical field.

BACKGROUND ART

In recent years, with the change in food life to European and American styles, large intestine cancer is remarkably increasing in Japan, too and the importance of large intestine examination has been rapidly recognized.

Nowadays, progress and propagation of diagnostic imaging by computed tomography (X-ray CT), ultra-sonography (US), magnetic resonance imaging (MRI), etc. are remarkable, and these diagnostic imagings have been also incorporated into the diagnostic region of tubular organs such as the large intestine. However, most of large intestine diseases stem from lesions occuring in mucosa, and for discovery of such lesions, as a matter of course, but also for grasping of detailed characteristics of the lesions, enema X-ray examination and endoscopy have been utilized as important means.

The enema X-ray examination methods known in the prior art may be broadly classified into the filling method, the double contrast method, the compression method, the mucosal relief method, etc., and according to the present standard of Ministry of Health and Welfare of Japan (reevaluation result), it is approved to use 200 to 2,000 ml of a 20 to 130 w/v % barium sulfate contrast medium.

Among these methods, since double contrast barium enema is optimum for imaging of lesions and diagnosis thereof, it holds the primary place in the current examinations.

The double contrast barium enema is a method, in which barium sulfate, a positive contrast medium, is coated as a thin layer on the inner walls of the large intestine, and air, a negative contrast medium, is simultaneously insufflated to inflate the large intestine, whereafter X-ray transmission is performed to image the state of the large intestine mucosa surface.

The double contrast barium enema includes the Fisher method (1923) in which an aqueous barium sulfate suspension with a concentration of about 40–50 w/v % is injected as a contrast medium after washing the intestine, the contrast medium is discharged out of the body and then air is insufflated before taking double contrast images; the Welin method (1953) in which after washing the intestine with quantities of water or enema as the primary treatment an aqueous barium sulfate suspension with a high concentration of about 100 w/v % is likewise charged into the intestine as a medium, the contrast medium is discharged out of the body and again a small amount of the contrast medium is injected with insufflation of air before taking double contrast images; and the modified Brown method (1963) in which the contents of the large intestine are removed without washing of the intestine by carrying out the preliminary treatment of application of strict diet control combined with administration of laxative, a barium sulfate contrast medium is charged into the intestine and double contrast images are taken without accompaniment of discharging of the barium sulfate contrast medium. Further, the modified Brown method has been improved so as to be well adapted for the Japanese and to give good double contrast images.

This modified Brown method is a method, in which after removal of the large intestine contents by injestion of low fat and low fiber meals (meals for contrast enema) combined with administration of laxative (saline laxative and contact evacuant), 200–300 ml of an aqueous barium sulfate suspension of a relatively higher concentration of about 60–80 w/v % is injected as a contrast medium into the intestine and, without being discharged, permitted to reach the deepest possible point of the large intestine by rolling the patient before insufflation of air for fluoroscopy or photographing. According to this method, it has become possible to visualize the state of the large intestine mucosa as fine network patterns.

Generally speaking, when a barium sulfate contrast medium which has been heretofore used in practice is used to conduct X-ray examination by double contrast method, if the concentration of barium sulfate used is low, the amount of barium sulfate coated is not enough to give good double contrast image, while as the concentration is higher, the amount coated on the intestinal mucosa is increased, but the coating of barium sulfate on the intestinal mucosa surface becomes too thick to give a fine network pattern, and also difficulty is frequently encountered in moving the contrast medium throughout the intestinal tract. For this reason, ordinarily, a barium sulfate contrast medium with a concentration of 60 to 80 w/v % has been used in X-ray examination by double contrast method.

In double contrast barium enema by use of a conventionally used contrast medium containing barium sulfate at a concentration of 60 w/v % or higher, due to X-ray intransmission at contrast medium pools which tend to be formed at flexures of bowels, imaging of intestinal walls is almost impossible, and further when another intestinal tract overlapping the intestine to be imaged in the X-ray direction by fluoroscopy exists, imaging of the overlapping intestinal portion is totally impossible.

For this reason, in order to perform diagnosis without overlookings, it is ideal to carry out examination of the whole large intestine with as small amount of contrast medium as possible (around 150 to 200 ml) so that no pooling may occur. However, since the large intestine extends with a complicated steric structure, a considerable skill is required for the technologist in delivering the injected contrast medium to the depths of the large intestine by way of rolling the patient.

Also for coating the contrast medium well on intestinal walls, it is necessary to conduct the rolling of the patient in different and in detailed manners, which means that the method imposes much burden on physically handicapped patients and aged people.

Further, as for the contrast medium coated on intestinal walls, thin layers thereof are cracked with lapse of time, it thus being necessary to complete photographing relatively quickly and hence a further skill of the technologist being demanded in order for these different requirements to be met.

With respect to the small intestine, such diseases as are peculiar thereto, for example, Crohn disease and malignant tumors, have recently come to be reported and the importance of small intestine examinations has been pointed out.

In the examination of the small intestine, X-ray examination is mainly employed because of the extreme difficulty of performing endoscopic examination in this case. The X-ray examination methods for the small intestine may be broadly classified into the oral administration method, the complete reflux small bowel examination and the peroral intubation method, among which the X-ray examination by double contrast method using the complete reflux small bowel method is considered best for the purposes of the diagnosis of organic lesions in the small intestine.

The peroral intubation method is a method in which a sound is inserted to the depths of the duodenum and a barium sulfate contrast medium and air are infused direct into the small intestine to obtain double contrast images. In this method is used a barium sulfate contrast medium comprising a barium sulfate aqueous suspension with a concentration of 50 to 70 w/v %. It is impossible to use such a barium sulfate contrast medium for the purpose of obtaining double contrast images all over the small intestine.

Thus, the small intestine consists of the jejunum and the ileum and its overall length is six to eight times that of the large intestine. Many flextures exist in the small intestine and there is a difference in the mucous membrane structure between the jejunum where villi are well developed and much mucilage is produced and the ileum where villi are not so well developed and mucilage is not produced so much. For these reasons, it is difficult to achieve homogeneous adhesion in the jejunum and the ileum with barium sulfate contrast media conventionally used in practice. Further, since these contrast media are subject to flocculation during passage through the intestinal tract, it is impossible to obtain homogeneous double contrast images all over the small intestine.

Furthermore, because of the peristalsis being strong in the jejunum and weak in the ileum, the movement of barium sulfate contrast medium in the intestinal tract is fast in the upstream portion and gets slower as the medium proceeds to the downstream portion of the small intestine. When the barium sulfate is used at a concentration of 40 w/v % or lower, the transfer in the intestinal tract gets faster but the coating ability is lowered with the result that no satisfactory double contrast images are obtainable. At concentrations higher than 40 w/v %, the flowability is lost to such an extent that the infused barium sulfate contrast medium reaches the ileocecal region with difficulty.

Due to the fact that the small intestine has many flexuous or overlapping portions, barium sulfate contrast medium pools tend to be formed when radiography of the small intestine X-ray examination by double contrast method is conducted by using a barium sulfate concentration of 50 to 70 w/v %, that is in the same manner as described above for the large intestine. No imaging of the intestinal walls at these contrast medium pools is possible because of X-rays being unable to be transmitted therethrough. Moreover, those intestinal portions overlapping these pools in the X-ray direction by fluoroscopy cannot be delineated.

Accordingly, attempts to conduct the small intestine X-ray examination by double contrast method lead to no satisfactory results. This method therefore needs to be supplemented by the compression method which, can be applied, to the jejunum but disadvantageously, not to the ileum because of anatomical differences.

OBJECT OF THE INVENTION

The object of the present invention is to provide a barium sulfate contrast medium for use in the X-ray examination by double contrast method of the large and small intestines, which is free, due to excellent flowability and hence enhanced movability in the intestinal tract and also to adequate X-ray transmissibility (radiolucency) and high coating ability, of the blind points in diagnosis as described above caused by contrast medium pools and overlaps therewith of intestinal portions and which obviates a high degree of technical skill that has been a drawback of the X-ray examination by double contrast method of the prior art.

The present inventors have previously found that when double contrast barium enema is carried out using an aqueous suspension containing barium sulfate at a low concentration of 15 to 35 % w/v and gum tragacanth at 2.0 to 0.5 % w/v, adequate X-ray transmissibility and high coating ability can be obtained and the blind points in diagnosis caused by contrast medium pools or overlaps therewith of intestinal portions eliminated thus to obviate the need for a high degree of technical skill and also computed tomography (X-ray CT) can be conducted immediately subsequent to the performance of the double contrast barium enema (JP, A, 2-85217; U.S. Pat. No. 5,160,724; EP, B1, 360266).

In the case of the above described barium sulfate contrast media in which gum tragacanth is used, however, the coating ability is enhanced at the sacrifice of a certain degree of flowability. It would therefore be more desirable if the flowability can be increased while maintaining the coating ability so as to conduct with more ease X-ray examination by double contrast method over the whole range of the large intestine.

Thus, an X-ray contrast medium using gum tragacanth has already been suggested (JP, A, 2-85217). In this case, however, the amount of gum tragacanth used needs to be increased if the coating ability of the contrast medium composition vis-a-vis the walls of the intestine is to be enhanced. What is worse, the more the amount of tragacanth used is, the less the flowability becomes.

As a result of extensive studies undertaken to seek a contrast medium equipped with satisfactory properties in respect of both coating ability and flowability, the present inventors have now found that when xanthan gum is used the flowability can be significantly ameliorated while maintaining the coating ability comparable to that attainable with gum tragacanth, and also that there exist optimum amounts of xanthan gum used for barium sulfate concentrations.

Thus, it has now been found that by using xanthan gum as the additive and increasing its amount in response to a decrease in the barium sulfate concentration the coating ability can be controlled with the result that excellent contrastability is attainable while maintaining satisfactory flowability.

It has also been found that the contrast medium developed as a result of the findings as described above can be used as extremely excellent contrast medium in computed tomography (X-ray CT) without formation of artifacts (artificial products) which is a barrier to diagnosis, because of its excellent coating ability which enables low concentrations of barium sulfate to be coated homogeneously on the walls of the intestinal tract.

Thus, the present invention provides an X-ray contrast medium for examination of the large and small intestines, which comprises an aqueous suspension containing 15 to 35 w/v % of barium sulfate and 0.6 to 0.15 w/v % of xanthan gum.

More particularly, the present invention provides an X-ray contrast medium for examination of the large and the small intestine comprising an aqueous suspension containing 15 to 35 w/v % of barium sulfate and 0.15 to 0.6 w/v % of xanthan gum, wherein when the barium sulfate concentration is in the range of 15 to 20 w/v %, the amount of xanthan gum used is in the range of 0.3 to 0.6 w/v %; when the barium sulfate concentration is in the range of 20 to 30 w/v %, the amount of xanthan gum used is in the range of 0.2 to 0.5 % w/v; and when the barium sulfate concentration is in the range of 30 to 35 w/v %, the amount of xanthan gum used is in the range of 0.15 to 0.4 w/v %, and wherein, in each case, the higher the barium sulfate concentration is, the smaller the amount of xanthan gum used is; and the lower the barium sulfate concentration is, the larger the amount of xanthan gum used is.

An example of X-ray contrast composition in which xanthan gum is used is known from the literature. Thus in JP, B, 54-34057, reference is made to an X-ray contrast composition using xanthan gum. The use of xanthan gum in the composition, however, is for the purpose of ameliorating the physicochemical stability of the barium sulfate in suspension, aiming at stabilization to gastric acid. Furthermore, the composition is for use in the filling method and uses, as described in the publication, 0.1 w/v % of xanthan gum for 20 w/v % of barium sulfate. With such a composition it is impossible to obtain double contrast images X-ray examination by double contrast method.

It is to be recognized in this context that the combination of barium sulfate concentrations and amounts of xanthan gum used is extremely characteristic, constituting an important element of the present invention.

Because of its excellent flowability, the contrast medium according to the present invention is extremely suitable for the small intestine X-ray examination by double contrast method by way of peroral intubation method.

Thus the contrast medium of the present invention is of good flowability, good movability in the intestinal tract, and good coating ability vis-a-vis both the jejunum and the ileum, and is subject to no flocculation, with the result that contrast medium pools formed are extremely few and hence satisfactory double contrast images can be obtained all over the small intestine.

Furthermore, even at contrast medium pools X-rays are adequately transmissible so that satisfactory images of the walls of the intestine can be obtained. In addition, those intestinal portions overlapping such pools in the X-ray direction by fluoroscopy can be delineated as sharp images, so that diagnosis can be performed for certain.

Furthermore, the contrast medium according to the present invention is extremely advantageous when used in diagnostic imaging by X-ray CT. Thus, the diagnostic imaging of large intestine diseases by computed tomography (X-ray CT) has been at present considered to be an essential examination in the pre-operative determination of disease stages. While examination by double contrast barium enema or endoscopy aims at imaging of fine lesions appearing on the large intestine mucosa surface, computed tomography (X-ray CT) is directed at grasping of the progressing state of lesions primarily on gastrointestinal walls or outside such walls, whereby information with regard to cancer such as information about the depth of wall invasion, invasion to adjacent organs, lymph node metastasis, peritoneal dissemination, remote metastasis (liver metastasis), etc. can be obtained, and therefore a high degree of diagnosis for large intestine cancer becomes possible by combination of these examination methods.

If computed tomography (X-ray CT) is to be performed after the examination by double contrast barium enema of the prior art, the contrast medium needs to be completely discharged prior to the performance of the X-ray CT examination, since those artifacts are otherwise produced in the resultant image by the contrast medium remaining within the intestinal tract, which interfere with diagnosis. The subsequent computed tomography (X-ray CT) is therefore obliged at present to be performed on a later date by way of the reflux large bowel examination with Gastrografin, the reflux large bowel examination with olive oil, the barium sulfate contrast medium infusion using barium sulfate at low concentrations of 5 w/v % or lower, etc. Where this is the case, the burden on patients increases and much more labor is needed in examination, due, for example, to the need of pretreating the patient again. Since the large intestine tends to move within the abdominal cavity, if computed tomography (X-ray CT) and double contrast barium enema cannot be conducted on the same day, the identification of lesional sites frequently becomes difficult. According to the contrast medium of the present invention, computed tomography (X-ray CT) can be performed immediately after double contrast barium enema, so that the affected part can be clearly delineated without formation of artifacts. Furthermore, since examination can be made with the minimum scanning while targeting those lesional sites identified by the preceding double contrast barium enema, the patient's burden and exposure to X-rays can be significantly reduced.

The present invention is described in more detail below.

The contrast medium according to the present invention comprises an aqueous suspension containing 15 to 35 w/v % of barium sulfate and 0.6 to 0.15 w/v % of xanthan gum. Xanthan gum can be produced by fermentation of carbohydrate using the Xanthomonas bacteria *Xanthomonas campestris,* followed by purification, drying and grinding. It is a polysaccharide composed mainly of the sodium, potassium and calcium salts of D-glucuronic acid, D-mannose and D-glucose, which is widely used in foodstuffs, cosmetics, pharmaceuticals etc. as a thicknet with resistance to acids, salts, heat and freeze. In the contrast medium according to the present invention, the xanthan gum concentration is dependent upon the barium sulfate concentration, and is increased as the barium sulfate concentration is decreased to a relatively low concentration.

Thus, for example, for barium sulfate concentrations of 15 to 20 w/v %, 0.6 to 0.3 w/v % of xanthan gum is incorporated; for barium sulfate concentrations of 20 to 30 w/v %, 0.5 to 0.2 w/v % of xanthan gum is incorporated; and for barium sulfate concentrations of 30 to 35 w/v %, 0.4 to 0.15 w/v % of xanthan gum is incorporated. In each of these combinations, the higher the barium sulfate concentration is, the smaller the amount of xanthan gum used is; and the lower the barium sulfate concentration is, the larger the amount of xanthan gum used is.

In order to finely delineate mucous membrane surfaces in X-ray examination by double contrast method and also to maintain that contrastability for a long period of time, gum arabic and/or sodium chondroitin sulfate may be added.

Gum arabic and/or sodium chondroitin sulfate may be used normally in amounts of 0.5 to 2.0 w/v %.

The contrast medium according to the present invention has excellent properties in respect of both flowability and coating ability. By conducting double contrast barium enema using 400 to 500 ml of the contrast medium the X-ray examination of the large intestine can be performed without a high degree of skill as required in the prior art. Furthermore, because of the adequate transmissibility of X-rays, diagnostic imaging becomes possible also in respect of contrast medium pools as well as intestinal sites in overlap therewith.

Furthermore, when large intestine cancer is found in double contrast barium enema, computed tomography (X-ray CT) can be performed immediately thereafter without formation of artifacts which interferes with diagnosis, and yet examination can be made with the minimum degree of scanning intended to image the lesional sites, whereby significantly efficient examination of the large intestine becomes possible.

In addition, since the contrast medium is coated on the entire mucous membrane surface of the large intestine in its extended state, not only identification of lesional sites of the large intestine can be performed with ease, but also the relationship between lesional sites and surrounding tissues can be clearly visualized.

Furthermore, due to its high coating ability and high flowability as well as its adequate radiolucency to X-rays, the contrast medium of the present invention is also useful in examining the small intestine which has a wider area to be examined and more overlapping portions than the large intestine. It also enables the X-ray examination by double contrast method of the small intestine by the peroral intubation method to be conducted with ease, and renders possible an extremely precise small intestine X-ray examination.

The contrast medium according to the present invention may contain different types of conventional additives, for example, dispersing agents such as sodium polyphosphate or the like condensed phosphates, wetting agents such as propylene glycol or polyethylene glycol, defoaming agents, preservatives, etc. It is also possible to simultaneously use gum tragacanth for adjustment of the coating ability. Also, for improvement of the dispersibility and coating film forming ability of barium sulfate, one or more kinds of suspending agents such as sodium carboxymethyl cellulose, carageenan, sodium alginate, methyl cellulose and gelatin.

The present invention is described in detail by referring to the following Examples.

EXAMPLE 1

In 95.6 liters of purified water were dissolved by heating 0.05 kg of benzoic acid and 0.05 kg of dehydroacetic acid, and 0.4 kg of xanthan gum and 0.8 kg of sodium chondroitin sulfate were then dissolved in the solution, whereafter 20 kg of barium sulfate was added, followed by sufficient mixing and dispersing by means of a homomixer etc.

The resultant suspension was sterilized by heating. After cooling 0.01 kg of silicone resin was aseptically added as a defoaming agent and the mixture was stirred well to give a contrast medium.

Specific gravity: 1.131

Viscosity: 48 mPa.s (shear rate 191.5 s$^{-1}$)

E-type rotation viscometer (Tokyo Keiki) Model EMD (cone plate 1.34')

Measurement temperature: 30° C.

Figure 1:
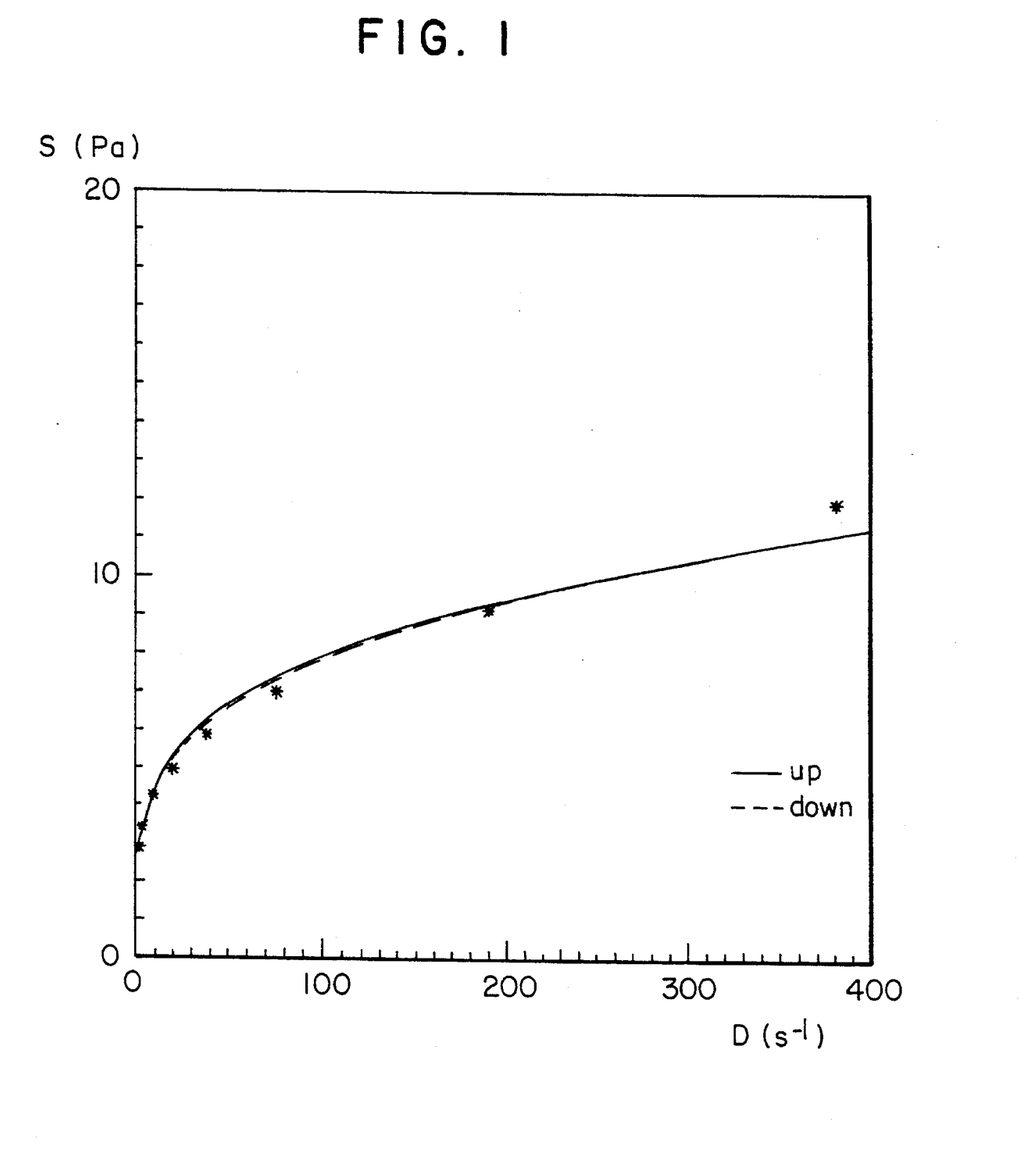
FIG. 1 is a graph showing the flow curve of the contrast medium of the present invention obtained in Example 1.

Flow curve is shown in FIG. 1.

Figure 2:
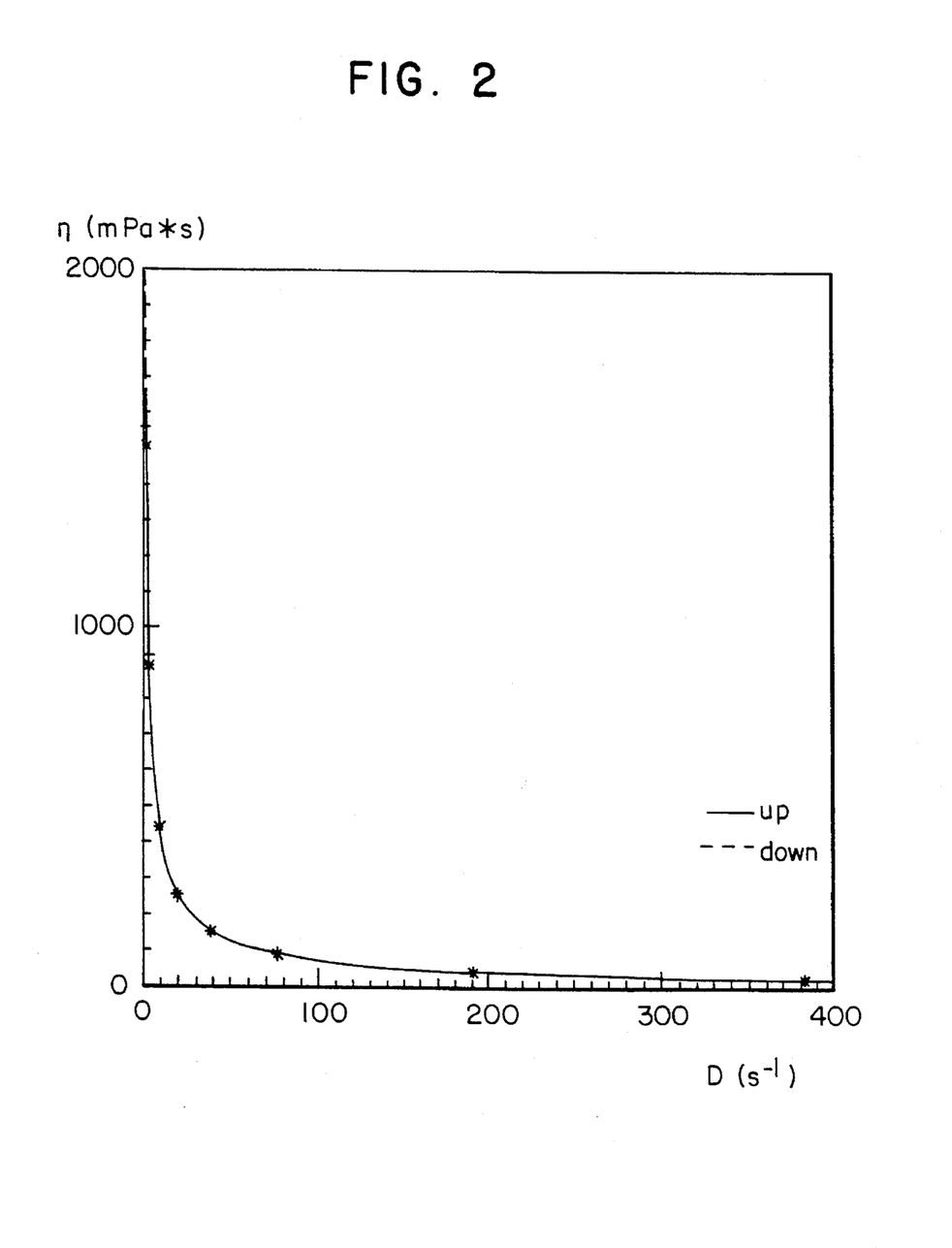
FIG. 2 is a graph showing the viscosity curve of the same contrast medium (Example 1)

Viscosity curve is shown in FIG. 2.

EXAMPLE 2

In 94.4 liters of purified water was dissolved by heating 0.05 kg of benzoic acid, and a solution of 0.02 kg of ethyl p-hydroxybenzoate and 0.01 kg of butyl p-hydroxybenzoate in 0.5 kg of propylene glycol was then added to the solution. After 0.35 kg of xanthan gum and 1.0 kg of gum arabic were dissolved therein, 25 kg of barium sulfate was added and the whole mixture thus obtained was mixed and dispersed using a homomixer.

The resultant suspension was sterilized by heating. After cooling, 0.01 kg of silicone resin was aseptically added as a defoaming agent and the mixture was stirred well to give a contrast medium.

Specific gravity: 1.184

Viscosity: 46 mPa.s (shear rate 191.5 s$^{-1}$)

E-type rotation viscometer (Tokyo Keiki) Model EMD (cone plate 1.34')

Measurement temperature: 30° C.

Figure 3:
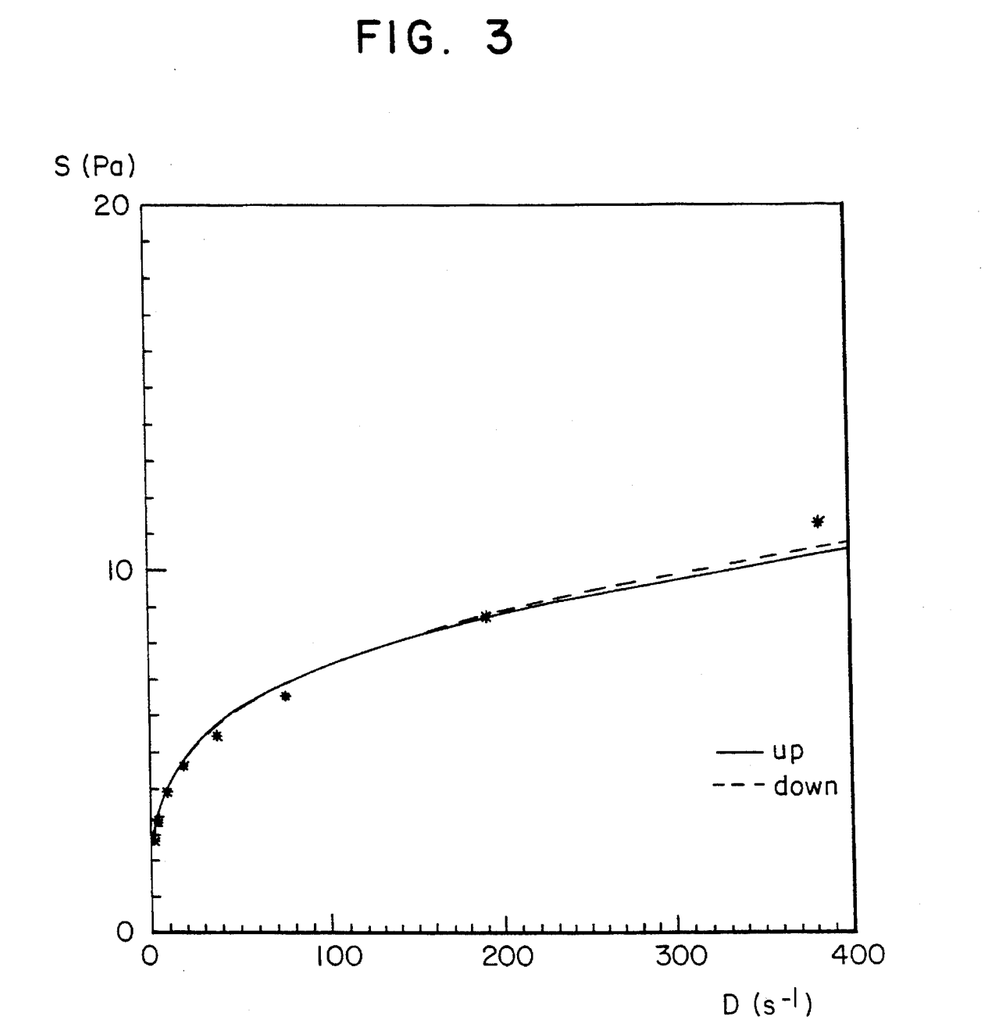
FIG. 3 is a graph showing the flow curve of the contrast medium of the present invention obtained in Example 2.

Flow curve is shown in FIG. 3.

Figure 4:
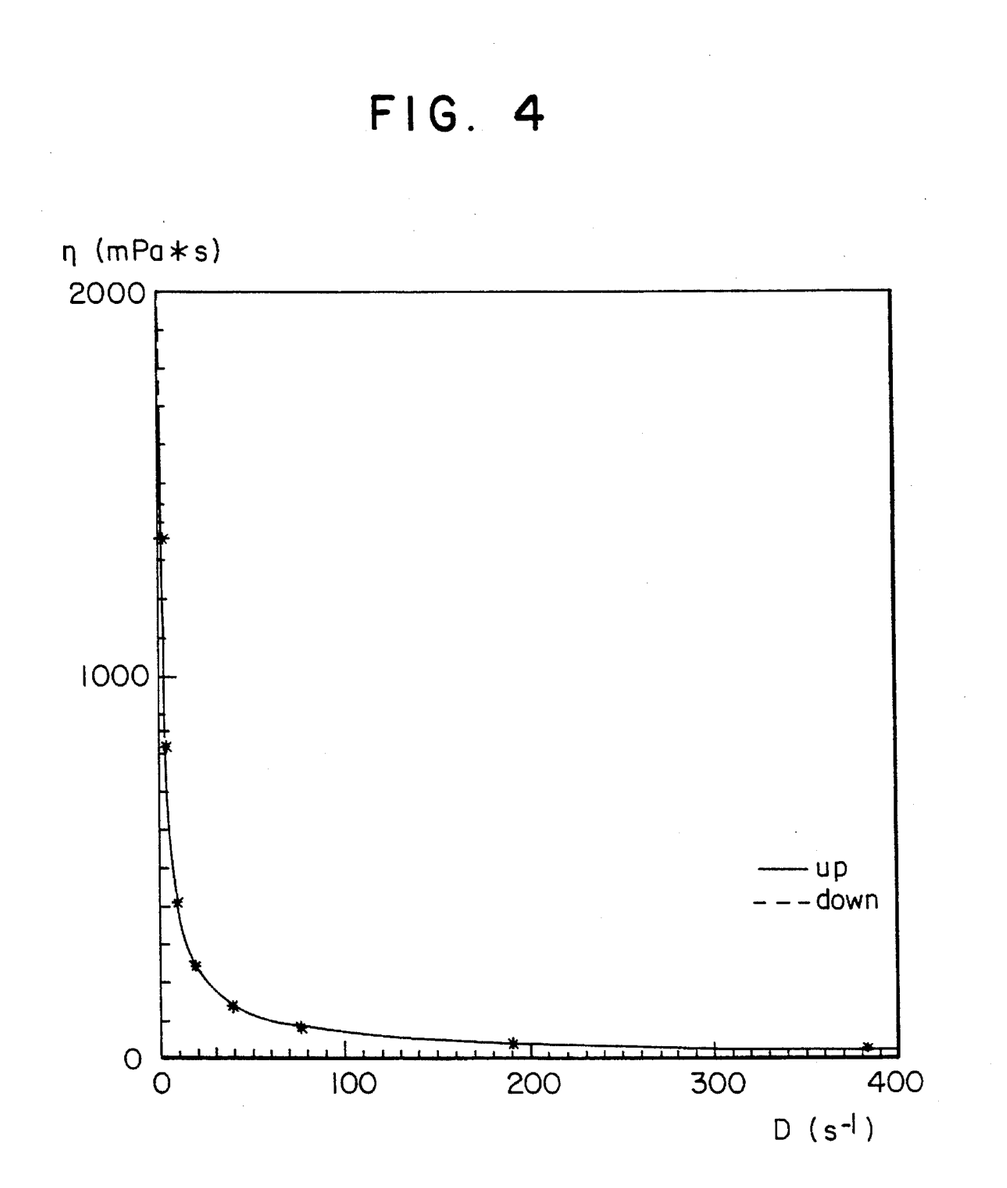
FIG. 4 is a graph showing the viscosity curve of the same contrast medium (Example 2)

Viscosity curve is shown in FIG. 4.

EXAMPLE 3

In 93.3 liters of purified water was dissolved 0.1 kg of sodium polyphosphate, whereafter 0.05 kg of benzoic acid was dissolved in the solution by heating. A solution of 0.02 kg of ethyl p-hydroxybenzoate and 0.01 kg of butyl p-hydroxybenzoate in 0.5 kg of propylene glycol was added to the solution. In the resultant solution were dissolved 0.3 kg of xanthan gum, 1.0 kg of gum arabic and 0.25 kg of sodium carboxymethyl cellulose, whereafter 30 kg of barium sulfate was added and the mixture was mixed and dispersed using a homomixer.

The resultant suspension was sterilized by heating. After cooling, 0.01 kg of silicone resin was aseptically added as a defoaming agent and the mixture was stirred well to give a contrast medium.

Specific gravity: 1.231

Viscosity: 36 mPa.s (shear rate 191.1 s$^{-1}$)

E-type rotation viscometer (Tokyo Keiki) Model EMD (cone plate 1.34')

Measurement temperature: 30° C.

Figure 5:
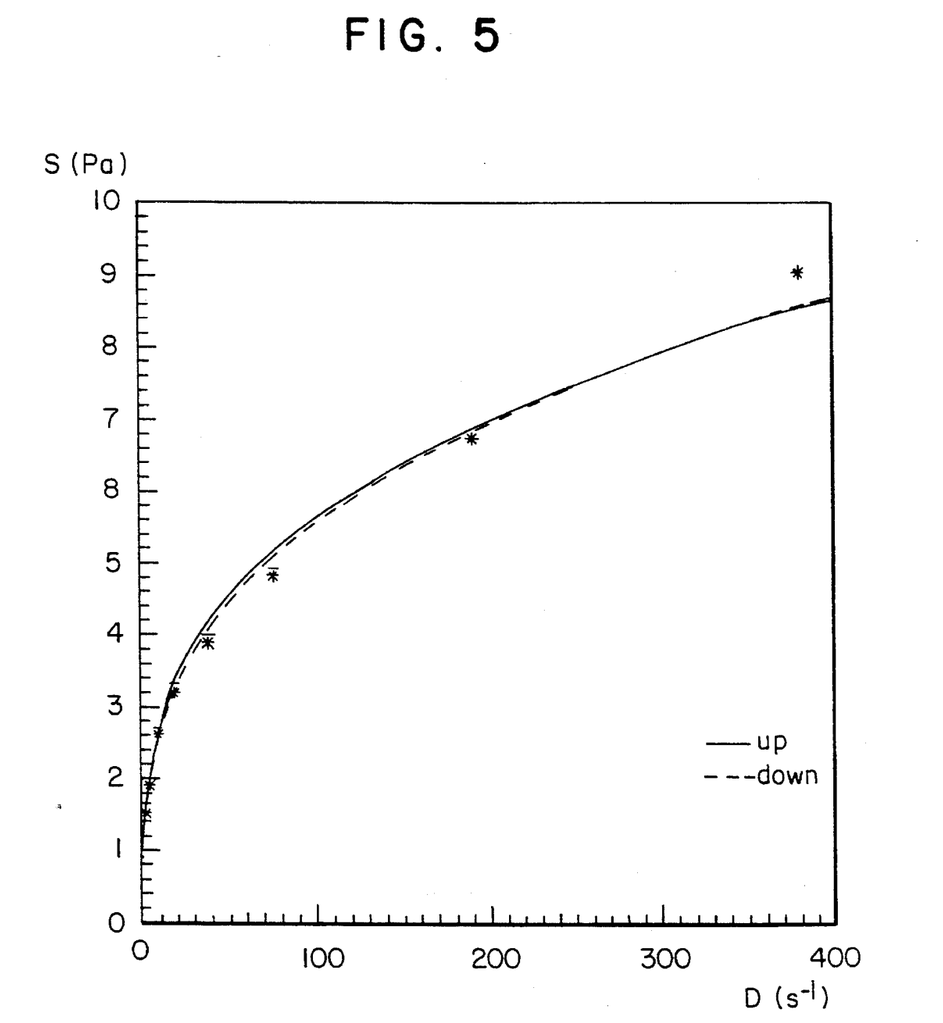
FIG. 5 is a graph showing the flow curve of the contrast medium of the present invention obtained in Example 3.

Flow curve is shown in FIG. 5.

Figure 6:
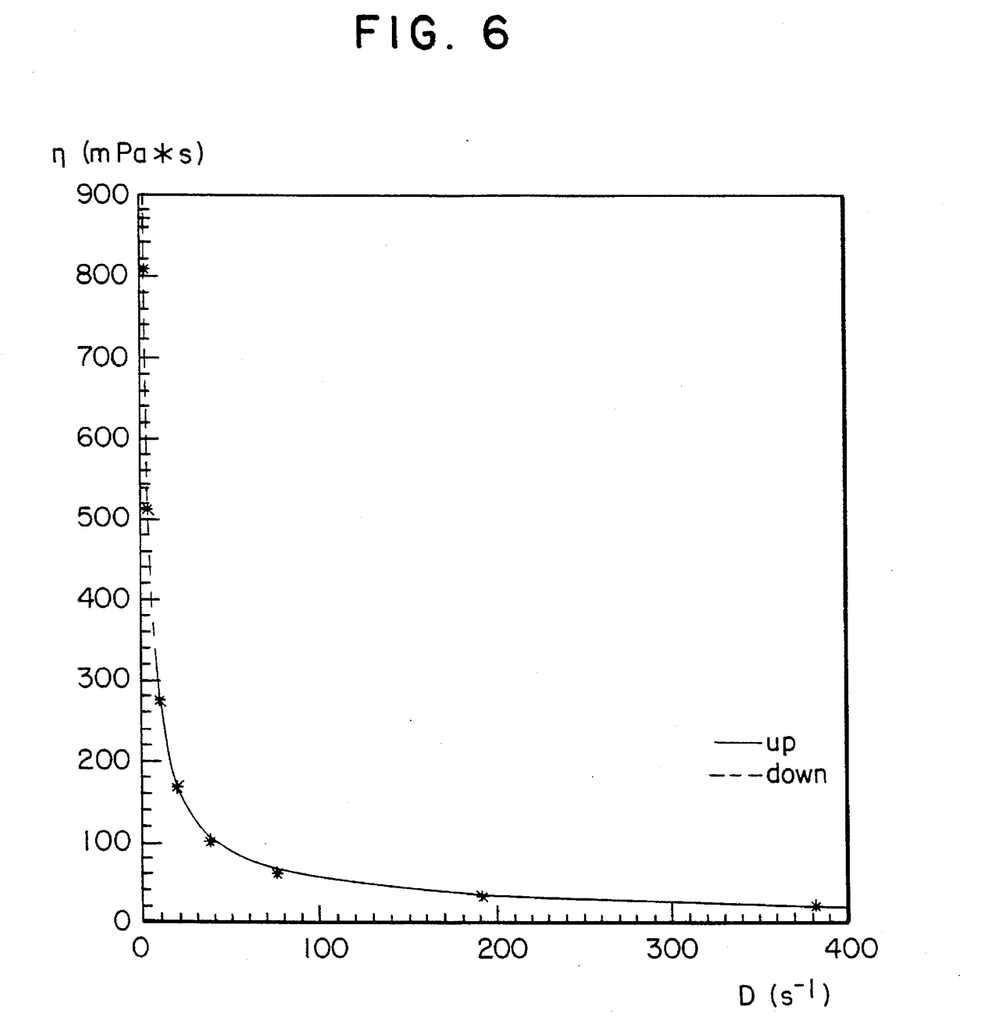
FIG. 6 is a graph showing the viscosity curve of the same contrast medium (Example 3)

Viscosity curve is shown in FIG. 6.

EXAMPLE 4

In 93.3 liters of purified water was dissolved by heating 0.05 kg of benzoic acid. A solution of 0.02 kg of ethyl p-hydroxybenzoate and 0.01 kg of butyl p-hydroxybenzoate in 0.5 kg of propylene glycol was dissolved in the solution. After 0.2 kg of xanthan gum, 0.4 kg of gum tragacanth, 0.5 kg of gum arabic and 0.5 kg of sodium chondroitin sulfate were dissolved therein, 30 kg of barium sulfate was added and the mixture was mixed and dispersed by means of a homomixer.

The resultant suspension was sterilized by heating. After cooling, 0.01 kg of silicone resin was aseptically added as a defoaming agent and the mixture was stirred well to give a contrast medium.

Specific gravity: 1.227

Viscosity: 61 mPa.s (shear rate 191.1 s$^{-1}$)

E-type rotation viscometer (Tokyo Keiki) Model EMD (cone plate 1.34')

Measurement temperature: 30° C.

Figure 7:
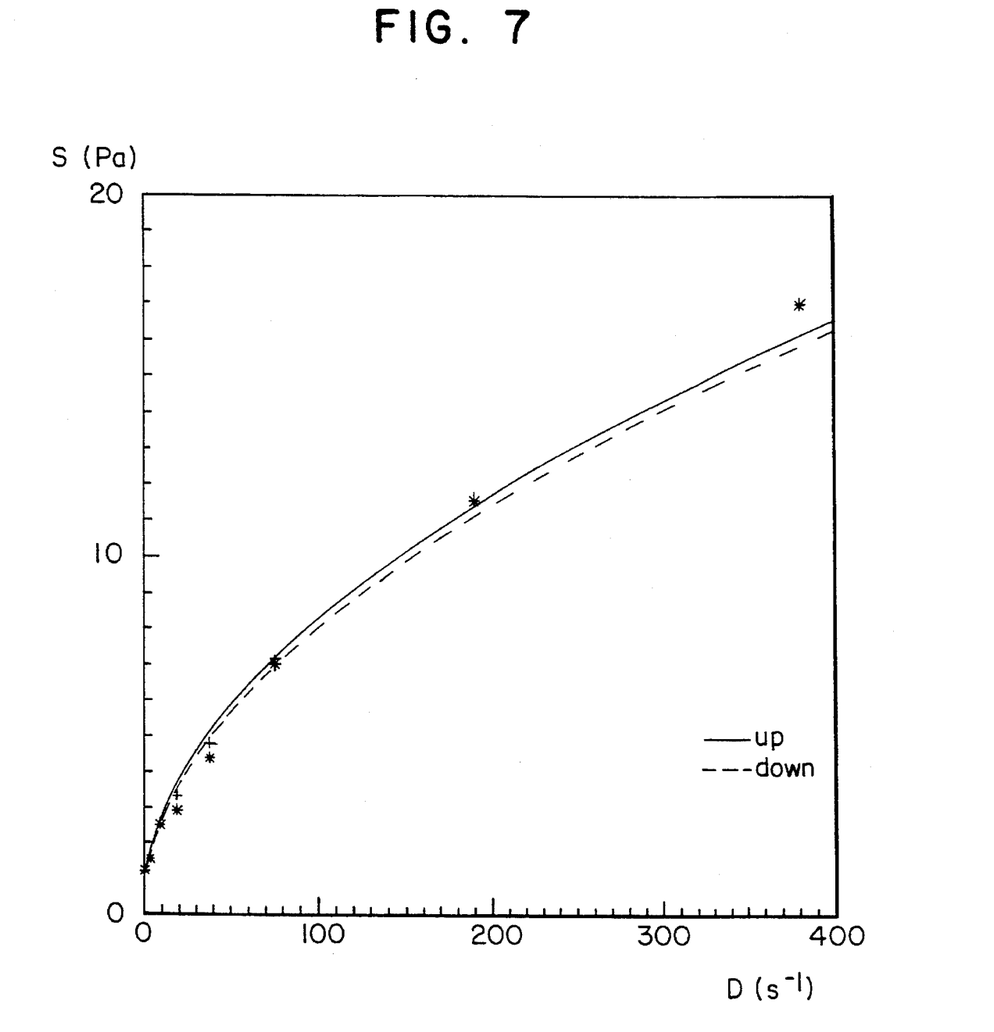
FIG. 7 is a graph showing the flow curve of the contrast medium of the present invention obtained in Example 4.

Flow curve is shown in FIG. 7.

Figure 8:
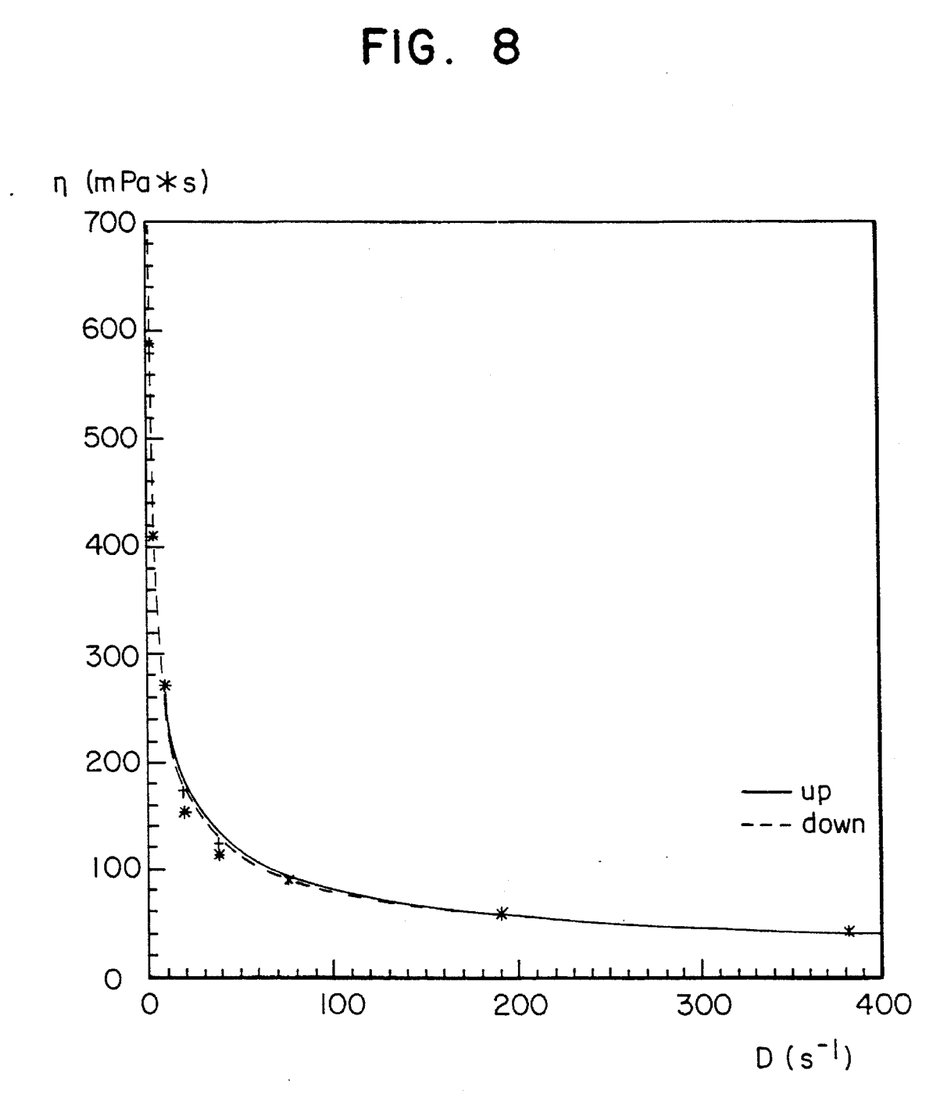
FIG. 8 is a graph showing the viscosity curve of the same contrast medium (Example 4 ).

Viscosity curve is shown in FIG. 8.

The clinical test evaluations in respect of different properties obtained with the respective contrast media prepared in Examples 1 to 4 are shown in the table below. For the pretreatment in these tests were used low residue food (enema food Colonoclean) and cathartics (125 ml of 13.6% magnesium citrate solution and 10 ml of 0.75% sodium picosulfate solution).

The contrastability was evaluated with 5 ranks of coating ability.

TABLE 1

| Evaluation contents | Example 1 | Example 2 | Example 3 | Example 4 |
|---|---|---|---|---|
| Double contrast barium enema | | | | |
| Contrastability | | | | |
| Rectum | +++ | +++ | +++ | +++ |
| Sigmoid colon | +++ | +++ | +++ | +++ |
| Descending colon | +++ | +++ | +++ | +++ |
| Transverse colon | +++ | +++ | +++ | +++ |
| Ascending colon | +++ | +++ | +++ | +++ |
| Ileocecum | +++ | +++ | +++ | +++ |
| Rolling of patient (coating, movement) | Possible at minimum limit | Possible at minimum limit | Possible at minimum limit | Possible at minimum limit |
| Burden on patient (rolling of patient, examination time) | Short with little burden | Short with little burden | Short with little burden | Short with little burden |
| Amount of contrast medium | Suitable at 400 ml | Suitable at 400 ml | Suitable at 400 ml | Suitable at 400 ml |
| Flowability | Extremely good | Extremely good | Extremely good | Extremely good |
| X-ray transmissibility | Very good | Good | Good | Good |
| Air bubble | Not recognized | Not recognized | Not recognized | Not recognized |
| Counterflow into the small intestine | None | None | None | None |
| Cracking | Not recognized for a long period | Not recognized for a long period | Not recognized for a long period | Not recognized for a long period |
| Double contrast imaging of the small intestine by direct peroral intubation method | Any one of the contrast media exhibited good intraluminal movability, uniform coating in both the jejunum and ileum and no occurrence of flocculation, thus permitting double contrast imaging of the whole small intestine. Satisfactory imaging is possible even at contrast medium pools and intestinal portions overlapping them because of adequate X-ray transmissibility being achieved there. | | | |
| Computed tomography (X-ray CT) | When used to perform double contrast barium enema followed immediately by X-ray CT examination, any one of the contrast media clearly delineated the relationship between the lesional sites and surrounding tissues without formation of artifacts which interferes with diagnosis. | | | |

N.B. Criteria for contrastability evaluation in barium enema
+++: readable and sharp image obtained
++: not sharp but readable image obtained
+: image partially unreadable, but sufficient for diagnosis obtained
±: no image of diagnostic value obtained
−: no image of possible use in examination obtained In the above-described double contrast barium enema tests, all the contrast media obtained in Examples 1 to 4 exhibited a good coating ability in the rectum, sigmoid colon, descending colon, transverse colon, ascending colon and ileocecum. They had an extremely high flowability in addition to such a high coating ability and gave sharp double contrast images of the whole large intestine with the minimum rolling of the patient. There were observed no cracking in the contrast medium coatings.

Although each of the contrast media of the Examples was used in a volume of as large as 400 ml, it was coated, for the most part, onto the intestinal walls with few pools formed to give satisfactory double contrast images over a wide range of the intestine. Even when a pool was formed, that portion did not give rise to any image that interfered with diagnosis due to adequate X-ray transmissibility being secured there.

When computed tomography (X-ray CT) was conducted subsequently to the double contrast barium enema, clear X-ray CT images without artifacts could be obtained, whereby identification of lesional sites could easily be made and the relationships between the lesional sites and the surrounding tissues could be clearly visualized.

Also when used in the X-ray examination by double contrast method of the small intestine by the peroral intubation method, the contrast media tested above exhibited a good movability in the intestinal tract as well as a uniform coating ability both in the jejunum segment and in the ileum segment. There was observed no flocculation which tends to take place in the jejunum and satisfactory double contrast images were obtained all over the small intestine. Even when a pool was formed, that portion did not give rise to any image that interfered with diagnosis due to adequate X-ray transmissibility being secured there.

EFFECTS OF THE INVENTION

By performing, after preliminary treatment with enema food and laxatives, double contrast barium enema by use of 400 to 500 ml of the contrast medium according to the present invention followed by computed tomography (X-ray CT), significant effects as shown below can be obtained as compared with the prior art.

Also in the X-ray examination by double contrast method of the small intestine by the peroral intubation method, significant effects as shown below can be obtained with the contrast medium of the present invention as compared with the prior art.

Double contrast barium enema examination:

1) Even in barium sulfate contrast medium-pooling portions, adequate X-ray transmissibility for the observation of mucosas and margins is secured in such a manner that the pools as well as intestinal portions overlapping them can be well observed. Thus the blind points in diagnosis can be eliminated.
2) Excellent movability in the intestine and excellent coating ability can be simultaneously achieved, thus requiring the subject to undergo no excessive rolling.
3) By use of an amount of 400 to 500 ml, movement of contrast medium to the depths of the large intestine is rendered possible and such rolling of the subject as would require the technologist to be skilled is obviated.
4) Due to minimized rolling of the subject, large intestine examination is rendered possible that alleviates burden on physically handicapped or aged subjects.
5) Notwithstanding the use of as much as 400 to 500 ml, there are formed few contrast medium pools and intraluminal double contrast images can be obtained over wide-ranging areas.
6) X-ray absorption difference within the range of imaging becomes smaller, whereby contrast can easily be controlled under X-ray photographing conditions to give very informative photographs.
7) Due to no excessive counterflow of contrast medium into the lower part of the small intestine, overlapping with the lower part of the large intestine can be prevented.
8) Times required for examination are remarkably shortened as compared with the prior art.
9) Due to good water-holding capacity, coated contrast medium layers do not crack over a long period of time.
10) Since the absolute amount of barium sulfate used is small, discharging after examination can be performed with ease.

Computed tomography (X-ray CT)

1) Immediately after double contrast barium enema, the examination of lesional sites can be conducted, and computer tomography (X-ray CT) can be performed without formation of artifacts (artificial products) which interferes with diagnosis.
2) Since computed tomography (X-ray CT) can be performed immediately after double contrast barium enema (hence while the contrast medium is coated onto all the internal circumferences of the whole large intestine in the extended state), the identification of lesional sites can easily be made and the relationship between the lesional sites and surrounding tissues can be clearly visualized.
3) Since lesional sites pointed out by double contrast barium enema examination can be immediately observed by computed tomography (X-ray CT), it becomes possible to perform examination with the minimum degree of scanning by relying on the lesional sites identified by the slit scanography as the targets, whereby the X-ray exposure to the patient can be greatly reduced.
4) Since double contrast barium enema and computed tomography (X-ray CT) can be performed continuously, no repetition of pretreatment is needed, thus reducing the burden on the subject and also significantly dispensing with time and labor required for examination.

X-ray examination by double contrast method of small intestine

1) Due to good intraluminal movability, uniform coating in both of the jejunum and ileum and no occurrence of flocculation, the contrast medium permits double contrast imaging of the whole small intestine.
2) There are formed few contrast medium pools and double contrast photographs can be obtained over wide-ranging areas of the small intestine. Even when such pools are formed, X-rays are adequately transmissible therethrough so that the pools as well as intestinal portions overlapping them can be observed. Thus the blind points in diagnosis can be eliminated.
3) Times required for examination are significantly shortened as compared with the prior art.

We claim:

1. An X-ray contrast medium for a double contrast enema examination of the large and the small intestine comprising an aqueous suspension containing 15 to 35 w/v % of barium sulfate and 0.15 to 0.6 w/v % of xanthan gum, wherein if the barium sulfate concentration is in the range of 15 to 20 w/v %, the concentration of xanthan gum is in the range of 0.3 to 0.6 w/v %; if the barium sulfate concentration is in the range of 20 to 30 w/v %, the concentration of xanthan gum is in the range of 0–2 to 0.5 w/v %; and if the barium sulfate concentration is in the range of 30 to 35 w/v %, the concentration of xanthan gum is in the range of 0.15 to 0.4 w/v %.

2. The X-ray contrast medium as claimed in claim 1, further comprising a member selected from the group consisting of gum arabic, sodium chondroitin sulfate, and a combination thereof.

3. The X-ray contrast medium as claimed in claim 2, wherein said gum arabic, sodium chondroitin sulfate, or a combination thereof is present in an amount of 0.5 to 2.0 w/v %.

4. A method for improving X-ray contrast images, which comprises administering to a patient the X-ray contrast medium according to claim 1, and transmitting X-rays through the X-ray contrast medium.

* * * * *